United States Patent [19]
Burns et al.

[11] Patent Number: 5,176,698
[45] Date of Patent: Jan. 5, 1993

[54] VENTED DILATATION CATHETHER AND METHOD FOR VENTING

[75] Inventors: Matthew M. Burns, Orono; Daniel O. Adams, Blaine; Charles L. Euteneuer, St. Michaels, all of Minn.

[73] Assignee: Scimed Life Systems, Inc., Maple Grove, Minn.

[21] Appl. No.: 639,132

[22] Filed: Jan. 9, 1991

[51] Int. Cl.⁵ ............................................. A61M 29/02
[52] U.S. Cl. ................................. 606/192; 606/194; 604/96
[58] Field of Search ................. 606/194, 192; 604/96, 604/103

[56] References Cited

U.S. PATENT DOCUMENTS

| | | | |
|---|---|---|---|
| 4,323,071 | 4/1982 | Simpson et al. | 128/343 |
| 4,606,347 | 8/1986 | Fogarty et al. | 128/344 |
| 4,638,805 | 1/1987 | Powell | 128/344 |
| 4,684,363 | 8/1987 | Ari et al. | 604/98 |
| 4,692,200 | 9/1987 | Powell | 156/289 |
| 4,715,378 | 12/1987 | Pope, Jr. et al. | 128/344 |
| 4,811,737 | 3/1989 | Rydell | 128/344 |
| 4,821,722 | 4/1989 | Miller et al. | 128/344 |
| 4,921,483 | 5/1990 | Wijay et al. | 604/96 |
| 4,943,278 | 7/1990 | Euteneuer et al. | 604/96 |
| 4,955,895 | 9/1990 | Sugiyama et al. | 606/194 |
| 4,964,853 | 10/1990 | Sugiyama et al. | 604/96 |

OTHER PUBLICATIONS

Yock, U.S. Patent application Ser. No. 852,197, entitled "Angioplasty Apparatus Facilitating Rapid Exchanges and Method," referenced in U.S. Pat. No. 4,748,982 issued Jun. 7, 1988.

*Primary Examiner*—Michael H. Thaler
*Attorney, Agent, or Firm*—Kinney and Lange

[57] ABSTRACT

A balloon dilatation catheter construction having an elongated shaft with a guide wire lumen and an inflation lumen therethrough, and a balloon member mounted on its distal end in combination with the inflation lumen where unwanted gases are vented from the balloon interior by first directing the gases proximally and thereafter directing the gases distally. Unwanted gases are directed proximally by a vent lumen which is sized to allow the unwanted gases to escape the balloon member while significantly inhibiting the flow of a purging medium therefrom. Thereafter, the gases are directed distally through the guide wire lumen where the gases are released from a distal end of the catheter.

37 Claims, 7 Drawing Sheets

VENTED DILATATION CATHETHER AND METHOD FOR VENTING

BACKGROUND OF THE INVENTION

The present invention relates to the field of angioplasty and in particular, to new and improved catheters for performing balloon angioplasty procedures on blood vessels.

Angioplasty has gained wide acceptance in recent years as an efficient and effective method for treating vascular diseases. Percutaneous transluminal angioplasty is widely used for the treatment of stenosis within the coronary arteries, and has been used for the treatment of stenosis in other areas of the vascular system.

The most widely used method of percutaneous transluminal angioplasty makes use of a dilatation catheter which has an inflatable balloon member at a distal end and an inner core containing a guide wire. The guide wire is threaded through the vascular system by tracking radiopaque coils contained at a distal tip which are monitored on an x-ray fluoroscope. Once the guide wire is positioned across the stenosis requiring treatment, the balloon member is advanced over the guide wire and positioned in the stenosis. The balloon member is subsequently inflated with liquid via an inflation lumen to exert pressure radially and outwardly against the lesion, causing the artery wall to stretch and reestablishing an acceptable blood flow through the artery.

Any air or other gases within the catheter must be purged before the catheter is introduced into the patient. One means for accomplishing this, as illustrated in U.S. Pat. No. 4,323,071, (Simpson, et al), is by incorporating a vent tube to direct the air and other gases proximally from the distensible balloon portion through the catheter so that the air or other gases are released outside the catheter at a proximal end thereof. A purging medium is introduced into the catheter whereby the air or other gases trapped within the balloon member are forced out through the vent tube. U.S. Pat. No. 4,715,378, (Pope, Jr., et al), discloses a gas purging arrangement where a catheter allows purging of air trapped within the balloon member by providing air passages in the windings of a coil located at the distal end of the catheter. U.S Pat. No. 4,821,722, (Miller et al), shows a catheter purging design wherein holes in the balloon member wall or in an interior surface of the inflation lumen allow the passage of air but are so small that the passage of inflation liquid therethrouqh is restricted.

The catheter purging arrangements described above have several disadvantages. One disadvantage is that it is often difficult to assure that all of the air trapped within the balloon catheter has been released. Furthermore, a larger profile catheter shaft is often required (e.g., to accommodate a purge tube) and the purging steps are often time consuming. Other disadvantages include difficulty in manufacture, high manufacturing expense and quality control. Therefore, there is a continuing need to provide an inexpensive balloon catheter that incorporates a quick and reliable method of purging the catheter of air.

SUMMARY OF THE INVENTION

The present invention relates to an improved multilumen balloon catheter which is easily and quickly purgeable of unwanted gases. In such a balloon catheter, which has a guide wire lumen, an inflation lumen and a distally placed balloon member with its interior in fluid communication with the inflation lumen, the improvement is a vent path which has a first proximally directed portion and a second distally directed portion, with the second portion defined by a distal segment of the guide wire lumen.

In a preferred embodiment of the present invention, the guide wire lumen has a proximal portion and a distal portion, with the proximal portion being defined by a first inner tube and the distal portion being defined by a second inner tube. The second inner tube is coaxially positioned within a distal section of the first inner tube to define an annular vent lumen therebetween. An outer tube is positioned over the first inner tube and extends coaxially therealong from a manifold to define an inflation lumen therebetween. The balloon member has a proximal portion connected to a distal end of the outer tube so that the balloon member interior is in fluid communication with the inflation lumen. The balloon member has a distal portion connected to a distal end of the second inner tube, which, during inflation, is spaced distally from a distal end of the first inner tube so that the balloon member interior is in communication with the vent lumen to form an inlet therefor. The vent lumen is sized to permit the flow of gas therethrough, while significantly inhibiting the flow of liquid therethrough.

The inventive method for purging the catheter of air begins by holding the balloon member in a vertical position with a distal end of the catheter in the most elevated position, and introducing a liquid inflation medium under pressure (greater than 1 atm, 14.7 psi) into the inflation lumen and subsequently into the balloon member, thereby forcing gases trapped within the inflation lumen and the balloon member through the inlet into the vent lumen. Gases are further forced out the vent lumen to an outlet in the guide wire lumen. The vent lumen becomes filled with inflation medium.

Once the balloon member is fully inflated with the inflation medium, it is inspected to ascertain whether it is functioning properly. A liquid purging medium is then introduced into the guide wire lumen to push the gas trapped within the guide wire lumen out a distal end of the guide wire lumen. The balloon member is subsequently deflated by pulling a vacuum through the inflation lumen. Because the pressure of the vacuum is less than the pressure used to inflate the balloon member, and because the inflation medium has a significantly higher viscosity than a gaseous medium which could be present within the vent lumen, the vacuum applied will result in an insignificant flow of liquid inflation medium from the vent lumen back into the balloon member.

Once these preparatory steps have been performed, the catheter is purged and ready to be inserted into the vascular system of a patient.

DETAILED DESCRIPTION OF THE PREFERRED EMBODIMENTS

Figure 1:
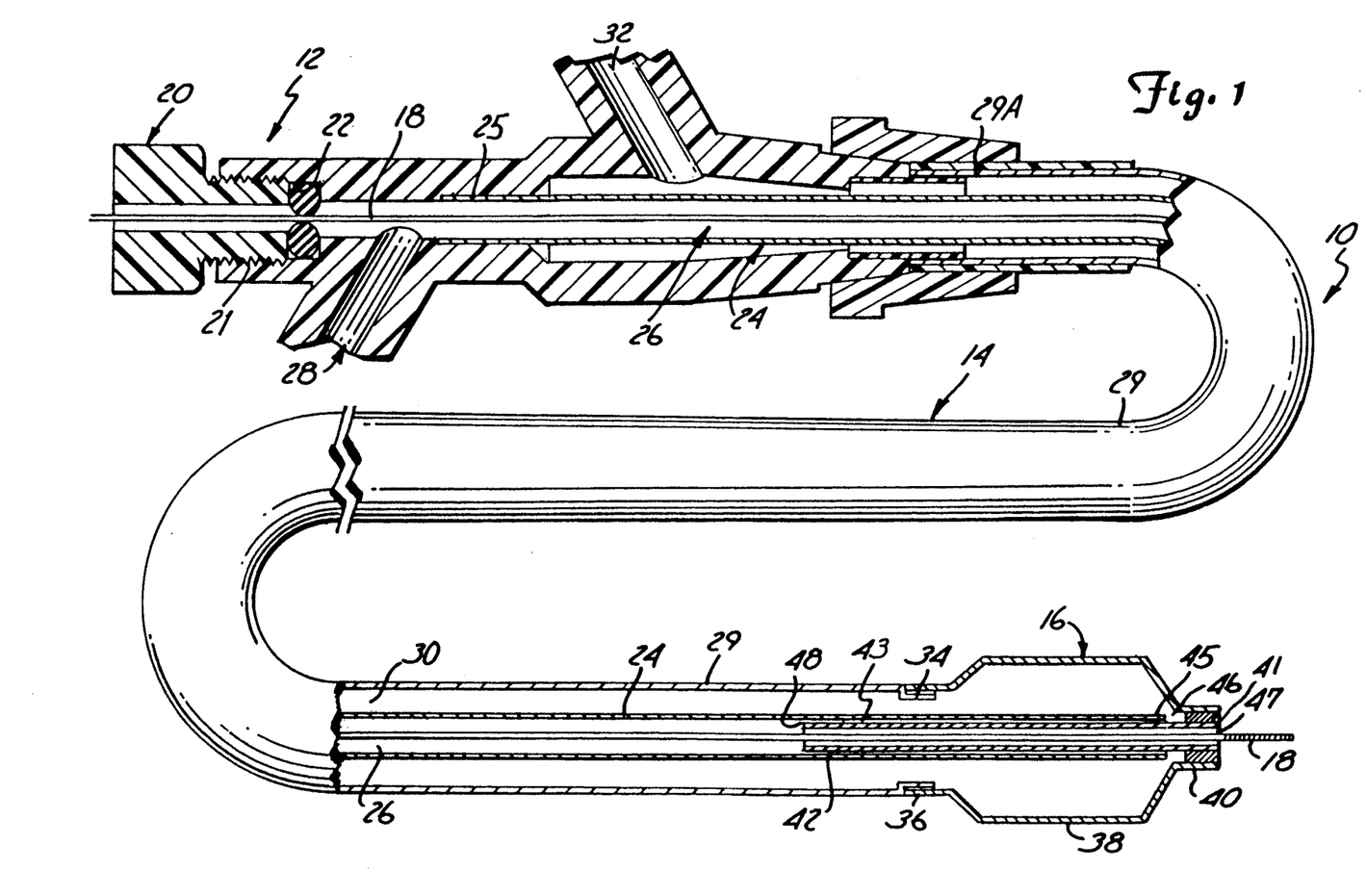
FIG. 1 is a side view, partially in section, of a balloon dilatation catheter of the present invention with a balloon shown in an inflated condition.
Figure 2:
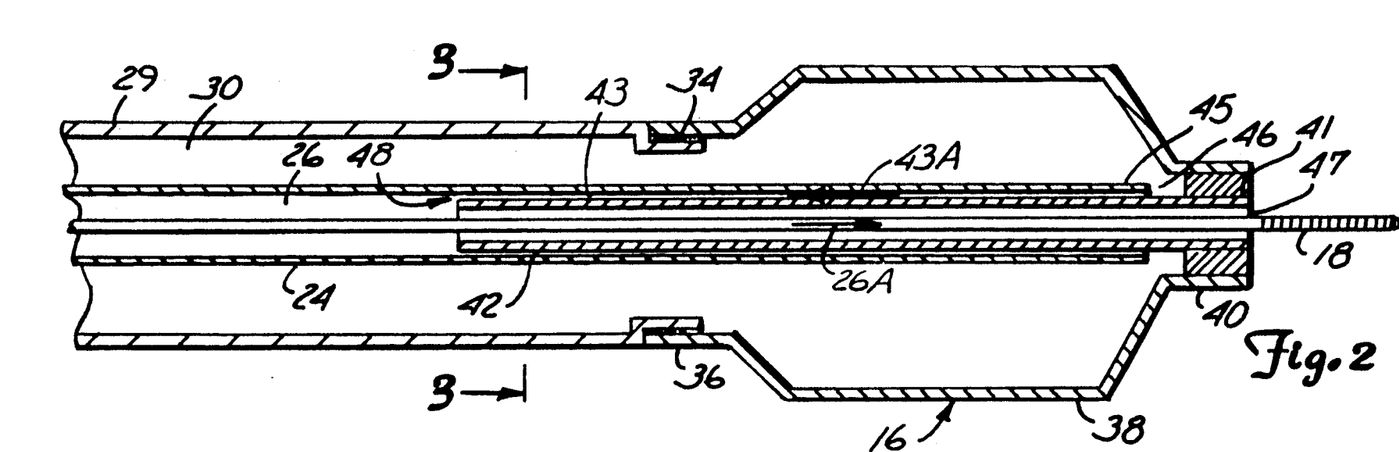
FIG. 2 is an enlarged side sectional view of a distal portion of the balloon dilatation catheter of FIG. 1 with the balloon shown in an inflated condition.
Figure 3:
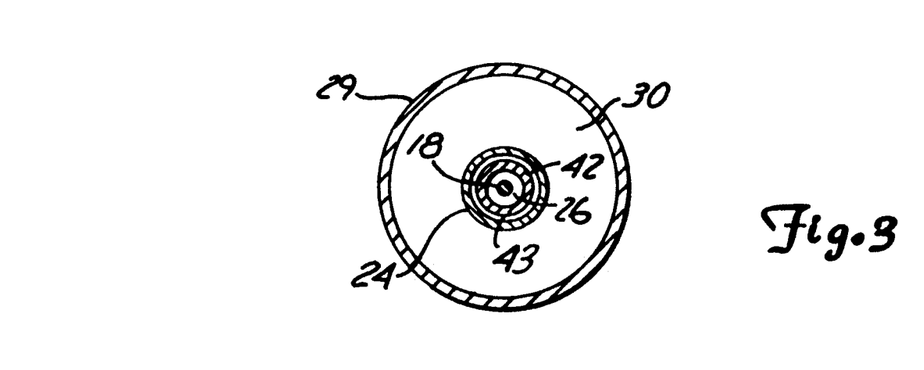
FIG. 3 is a sectional view as taken on line 3—3 of FIG. 2.

Catheter 10, as shown in FIGS. 1, 2 and 3, is a balloon dilatation catheter which includes a manifold 12, a shaft 14, a balloon member 16.

Manifold 12, defining a proximal portion of catheter 10, is an elongated rigid member, preferably formed of an inflexible plastic material. A thumbscrew 20 is threadably mounted on a threaded proximal end of manifold 12 and is used to fix the position of a guide wire 18 interposed therethrough. Screwing the thumbscrew 20 onto the manifold 12 applies pressure to a deformable member (O-ring 22) which constricts onto the guide wire 18, and thus restricts longitudinal movement of the guide wire 18 relative to the manifold 12 and catheter 10 and provides a fluid seal between the manifold 12 and guide wire 18.

A first inner tube 24, which is preferably formed from a plastic material such as polyethylene, is disposed at a proximal end 25 within a central bore of manifold 12 and is attached thereto. The inner tube 24 extends distally therefrom to define a guide wire lumen 26 for the guide wire 18 to direct the catheter through the patient. An inner surface of the first inner tube 24 is preferably coated with a lubricous material, such as polytetrafluoroethylene or polydimethylsiloxane, to facilitate movement of the guide wire 18 therethrough.

The manifold 12 has a purge port 28 between the O-ring 22 and the proximal end 25 attachment of the first inner tube 24, adapted for connection to a fluid delivery device (not shown) such as a syringe which provides fluid under pressure to the guide wire lumen 26. The O-ring 22 provides a fluid seal at a proximal end of the guide wire lumen 26 when the thumbscrew 20 is tightened.

The shaft 14 is defined by an outer tube 29 which is attached at a proximal end 29A to the manifold 12 within a central bore thereof and extends coaxially with and along the inner tube 24. An annular balloon inflation lumen 30 is defined between the coaxially extending outer tube 29 and the first inner tube 24. The manifold 12 has a balloon member inflation port 32 adapted for connection to an inflation device (not shown) which provides fluid under pressure to the balloon member 16 via the inflation lumen 30.

The outer tube 29 is an elongated flexible elastic tube, preferably formed of polyethylene. An outer surface of outer tube 29 has a lubricous coating, such as polytetrafluoroethylene or polydimethylsiloxane, which provides a slippery surface to aid with the insertion of the catheter 10 through a guide catheter within a patient and removal therefrom. At a distal end 34, outer tube 29 has a section of reduced diameter to which a proximal lip segment 36 of balloon member 16 is attached, preferably by an adhesive seal such as epoxy. The first inner tube 24 extends beyond the distal end 34 of outer tube 29 into the balloon member 16, as seen in FIG. 1.

The balloon member 16, which is preferably formed from a polymer material such as polyolefin copolymer, has a proximal lip segment 36 as described, a distensible balloon member segment 38 and a small diameter distal segment 40. The distal segment 40 of the balloon member 16 is bonded to a distal end 41 of a second inner tube 42, also preferably by an adhesive such as epoxy. The second inner tube 42 is also preferably formed from a flexible material such as polyimide or alternatively, polyethylene, and has a lubricous coating on its inner surface such as polytetrafluoroethylene or polydimethylsiloxane. The second inner tube 42 is of smaller diameter than the first inner tube 24 and extends proximally from the distal end 41 thereof through the first inner tube 24. The second inner tube 42 extends coaxially along the first inner tube 24, preferably as far as or beyond the lip segment 36 of the balloon member 16 and the distal end 34 of the outer tube 29. The second inner tube 42 thus defines a distal portion of the guide wire lumen 26 while the first inner tube 24 defines a proximal portion thereof. Because the second inner tube 42 is within the first inner tube 24, the guide wire lumen 26 has a smaller diameter along the distal portion thereof (the length of the second inner tube 42). An annular vent lumen 43 is defined by the coaxial alignment of the first and second inner tubes 24 and 42, to provide a path for air or gas to escape from the balloon member 16 to the guide wire lumen 26 when pressurized fluid is introduced into the balloon member 16 from the inflation lumen 30. The length of the vent lumen 43 is long enough so that it significantly inhibits the flow of the pressurized liquid therethrough but allows the unwanted gas to be forced into the guide lumen 26 to be purged out the distal end opening 47 of the catheter 10.

Figure 4:
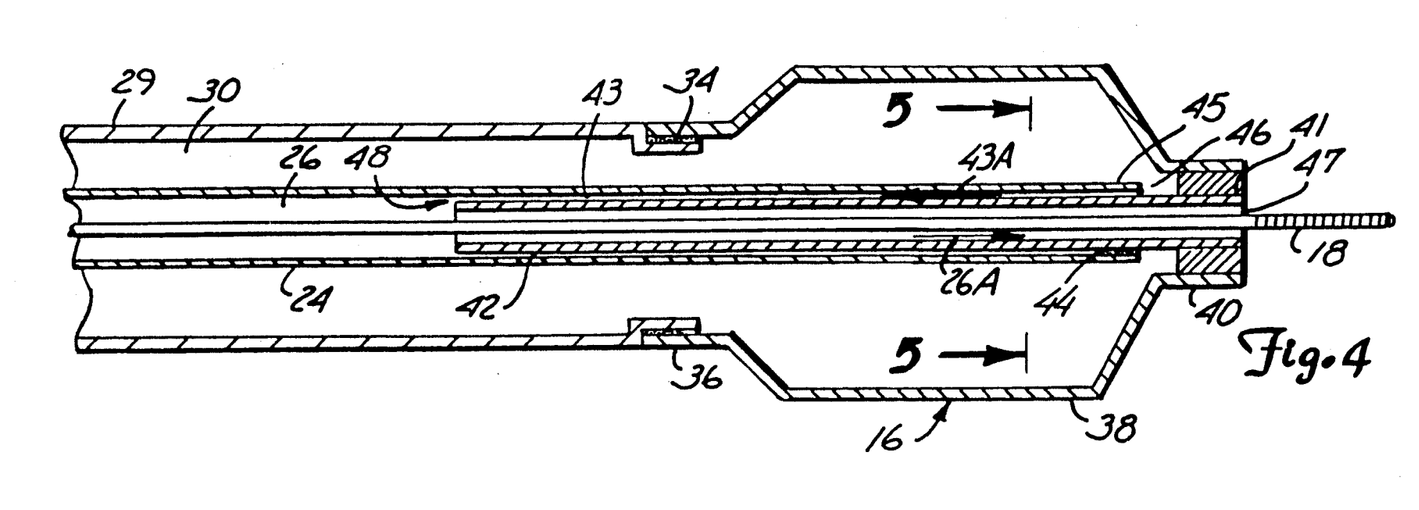
FIG. 4 is an enlarged side sectional view of a distal portion of a slightly different embodiment for the balloon dilatation catheter of FIG. 1 with the balloon shown in an inflated condition.
Figure 5:
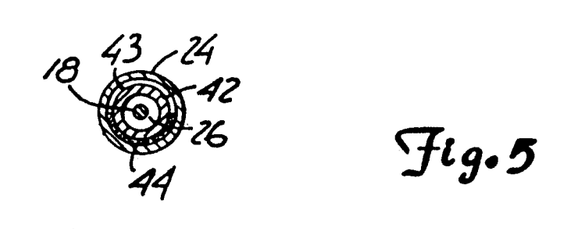
FIG. 5 is a sectional view as taken on line 5—5 of FIG. 4, with the balloon not shown for clarity.

FIGS. 4 and 5 illustrate a slightly different embodiment of catheter 10. In this embodiment, all like elements are numbered the same as in FIGS. 1-3. The only structural difference is that a partially circumferential adhesive bond 44 is provided between the first inner tube 24 and the second inner tube 42 at a distal end 45 of the first inner tube 24 leaving an opening in the bond 44 for an inlet to vent lumen 43. The connected inner tubes 24 and 42 thus form a continuous guide wire lumen structure from the manifold 12 to the distal end of the catheter 10. This construction provides the catheter with greater push from the proximal end to the distal end to help negotiate tortuous arteries since force can be transmitted by the bonded inner tubes to the distal end of the catheter.

During inflation of the catheter 10 (FIGS. 1-5), the distal end 45 of the first inner tube 24 is spaced from the distal segment 40 of the balloon member 16 to define an inlet 46 to the vent lumen 43. The outlet from the vent lumen 43 is entry port 48, which places the vent lumen 43 in fluid communication with the guide wire lumen 26. As contemplated, this arrangement defines a vent path that extends first proximally, (arrow 43A, FIG. 3 or 5), then distally, (arrow 26A, FIG. 3 or 5), to purge gas from the balloon member 16 and the inflation lumen 30 of the catheter 10. That is, the proximally extending portion of the vent path is defined by lumen 43 and the distally extending portion of the vent path is defined by the distal portion of the guide wire lumen 26. Thereafter, unwanted gas is finally purged from the catheter 10 through the distal end opening 47 of the guide wire lumen 26.

The inventive method for purging the balloon member 16 of air begins prior to introducing the catheter 10 into a patient. To prepare the catheter for use, an inflation medium is introduced through the inflation lumen 30 via inflation port 32, and into the balloon member 16 while holding the distal tip of the catheter in a most elevated position so that air is forced into the inlet 46. The continuous flow of inflation medium therethrough forces gases trapped within the inflation lumen 30 and balloon member 16 through the inlet 46 and into the vent lumen 43.

Specifically, the balloon member 16 is inflated with liquid delivered under a specified pressure, which would depend upon the rating of the particular balloon member type and would normally be between 2 and 10 atms (29.40 psi -147 psi). The inflation forces any air trapped within the balloon member 16 into the inlet 46 and through the vent lumen 43. Preferably, the dimensions of the inlet 46 and the vent lumen 43 are such that the flow of a fluid having a viscosity of less than approximately 0.02 centipoise (cps) (such as air) is readily allowed, while the flow of fluids having viscosities greater than 1.0 cps (such as the desired inflation liquids) is substantially restricted when the driving pressure therefore between the inlet 46 and the entry port 48 is in the range of 2 to 10 atm (29.40 psi -147 psi). Thus, air and a small plug of inflation liquid will enter the vent lumen 43 from the interior of the balloon member 16. During pressurization of the balloon member 16, all but perhaps an insignificant amount of air in the vent lumen 43 is pushed out of the vent lumen 43 (through entry port 48) into the guide wire lumen 26.

After the balloon member 16 is fully inflated, the physician inspects the balloon member 16 to ascertain whether it is functioning properly, for example, whether it is holding the appropriate amount of pressure and has no significant leaks. A purging medium is then introduced into the guide wire lumen 26 via the purge port 28, pushing any air trapped within the guide wire lumen 26 out the distal end opening 47 of the guide wire lumen 26.

Once the air trapped within the guide wire lumen 26 has been forced out of the catheter 10, the balloon member 16 is deflated by pulling a vacuum through the inflation device (not shown) to collapse the balloon member 16 around the first inner tube 24 to provide a deflated balloon member profile for insertion into the vascular system of the patient.

The advance of inflation medium into vent lumen 43 is controlled by several factors. First, the flow of the inflation medium is restricted by the small size of the vent lumen 43 and to an extent by the size of the inlet 46. Second, the inflation medium has a significantly higher viscosity than the gases forced into the vent lumen 43. In addition to these factors, the pressure drop of the vacuum across the vent lumen 43 is less than the pressure increase exerted while inflating the balloon member 16. Therefore, gases forced out of the inflation lumen 30 or balloon member 16 and into the vent lumen 43 are not likely to be drawn back into the balloon member 16 by the application of the vacuum.

The inlet 46 may be defined by alternative constructions. One such construction for inlet 46 (as shown in FIGS. 1, 3 and 4) is defined by the placement of the distal end 45 of the first inner tube 24 some distance from the distal segment 40 of the balloon member 16 (as shown with clarity in FIGS. 2 and 4). Alternatively, the distal end 45 of the first inner tube 24 may abut the distal segment 40 of balloon member 16. Consequently, the inlet 46 to vent lumen 43 is created either by holding the catheter 10 at or near a distal portion of the outer tube 29 (such as at the distal end 34) and pulling the distal segment 40 of the balloon member 16 in a distal direction relative to the outer tube 29 or, alternatively, the inlet 46 is created when the pressure of the inflation medium forced through the balloon member 16 forces the distal segment 40 of the balloon member 16 longitudinally away from the distal end 45 of the first inner tube 24.

In an example construction of catheter 10 (FIGS. 1-5), the first inner tube 24 made from polyethylene has an inner diameter of 0.020 inches and an outer diameter of 0.023 inches, while the second inner tube 42 made from polyethylene has an inner diameter of 0.016 inches and an outer diameter of 0.019 inches. Thus, by aligning the second inner tube 42 coaxially within the first inner tube 24 an annular vent lumen 43 is defined by the 0.001 inch diametrical spacing between an outer surface of the second inner tube 42 and an inner surface of the first inner tube 24. Preferably, the distance from the distal end 45 (adjacent inlet 46) of the first inner tube 24 to the proximal end of the second inner tube 42 (adjacent entry port 48) is approximately 15 centimeters (5.9 inches), thus defining the length of the vent lumen 43.

Using a 50% renografin ®-76(available from E. R. Squibb & Sons, Inc., Princeton, N.J.)/50% saline inflation medium (which has a viscosity of 2.5 centipoise (cps)), and an applied inflation pressure of 147 psi (10 atm), the flow rate of the inflation solution through the vent lumen 43 and out entry port 48 would be approximately 0.0025 cubic centimeters per second. Contrastingly, air having a viscosity of less than 0.02 centipoise (cps) will flow out the vent lumen at a rate of 0.31 cubic centimeters per second under a similar driving pressure of 147 psi (10 atm). Thus, the time to evacuate air from the interior of the balloon member 16 and inflation lumen 30 (where the inflation lumen has a volume of approximately 0.50 cubic centimeters and which has a 3.0 mm (0.1183 inches) diameter and 2.0 cm (0.788 inches) long dilatation balloon with an inflated interior volume of 0.12 cubic centimeters) through the vent lumen 43 would be approximately two (2) seconds.

As can be appreciated, a flow rate of 0.002 cubic centimeters per second of fluid through the vent lumen is relatively insignificant. In addition, the pressure differential created by the vacuum pulled to deflate the balloon member prior to insertion into the patient's body is proportionally much less than or equal to (1 atm or 14.7 psi) an inflation pressure in the range of 2 to 10 atm (29.40 psi -147 psi), that the "small plug" of inflation medium in the vent lumen 43 is not readily pulled back into the interior of the balloon member. Also, it can be appreciated that upon the initial application of an inflation pressure, the gases in the balloon member 16 and inflation lumen 30 are quickly and efficiently forced into and through the vent lumen 43 and thereafter forced out the distal end opening 47 of the guide wire lumen 26. Of course, providing a bond between the first inner tube 24 and second inner tube 42, as illustrated in FIGS. 4 and 5, reduces the cross-sectional area available for the vent lumen 43 (proximate to the inlet 46 therefor) to further inhibit the flow rate of gases and inflation medium therethrough. Proportionately, however, the relative flow rates of gases and inflation medium will remain the same, permitting gases to travel through vent lumen 43 more readily than the inflation medium as described.

Figure 6:
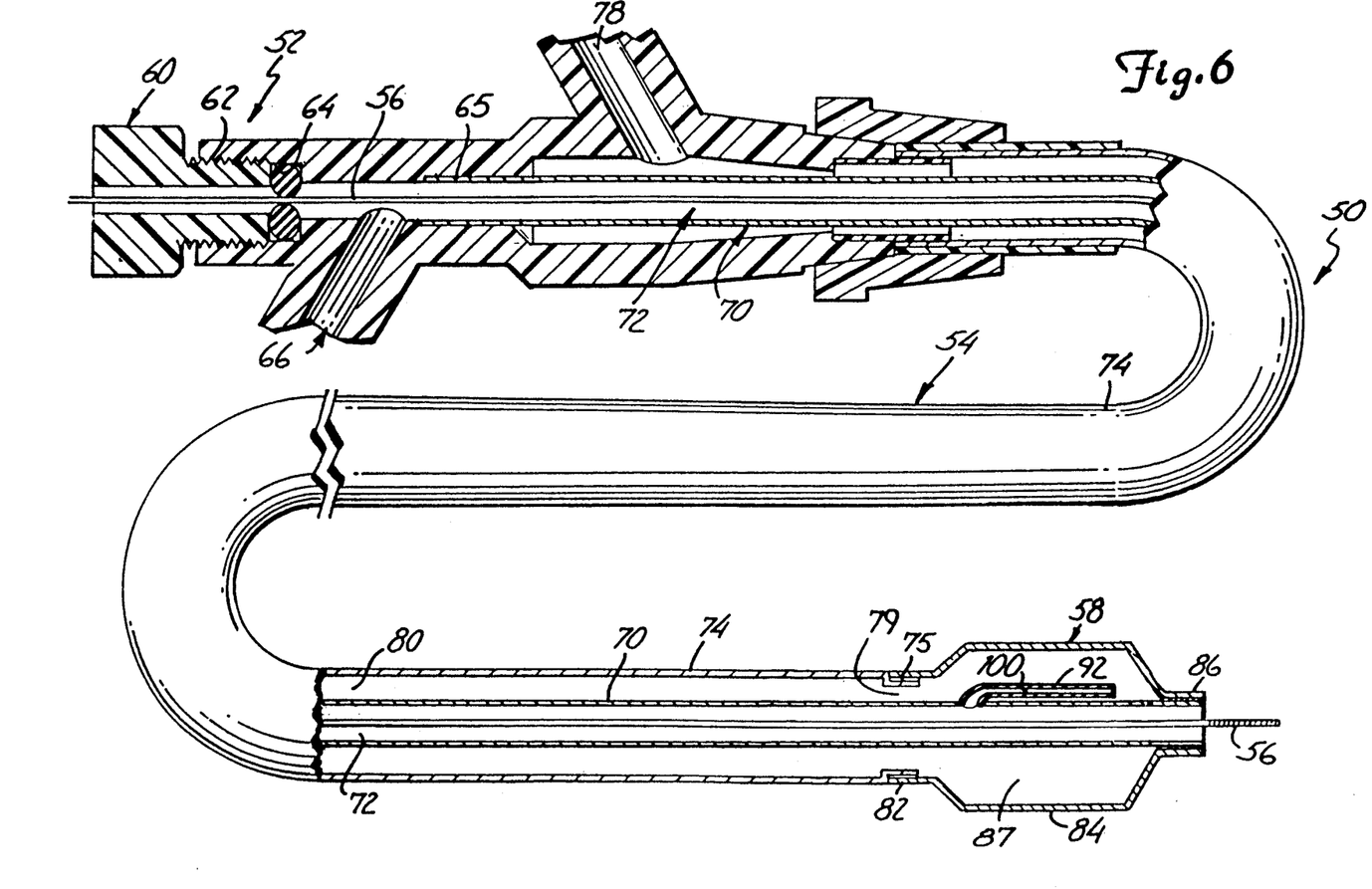
FIG. 6 is a side view, partially in section, of another embodiment of the balloon dilatation catheter of the present invention with a balloon shown in an inflated condition.
Figure 7:
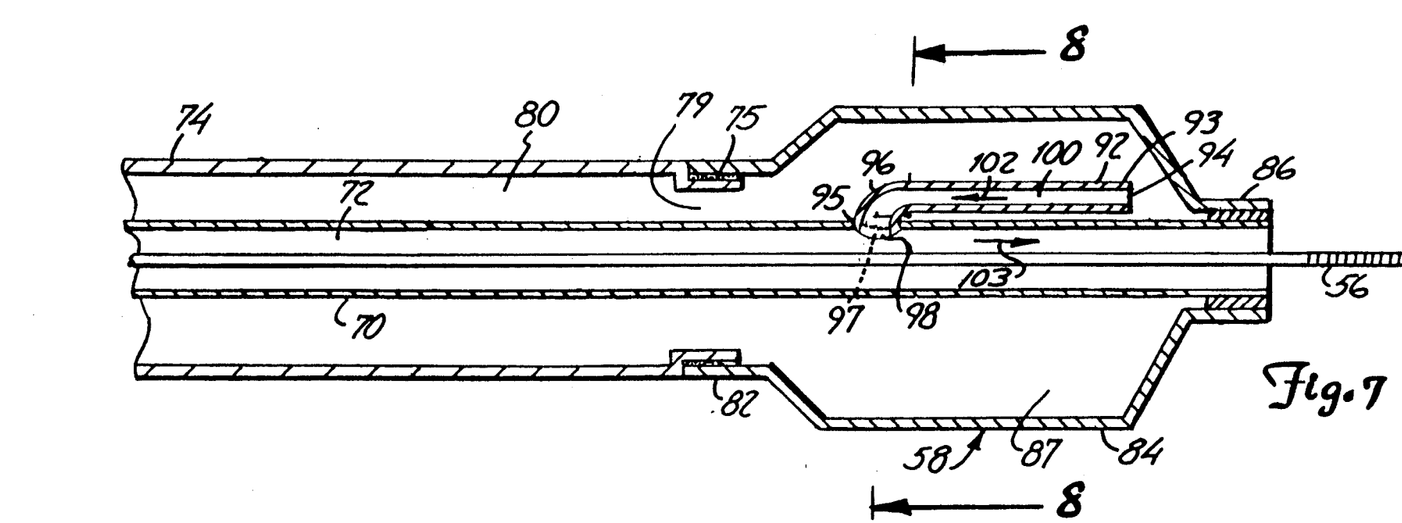
FIG. 7 is an enlarged side sectional view of a distal portion of the balloon dilatation catheter of FIG. 6 with the balloon shown in an inflated condition.
Figure 8:
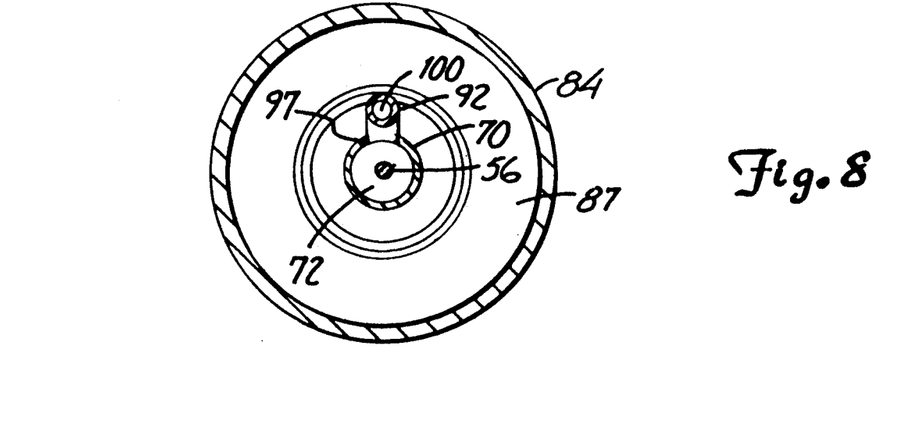
FIG. 8 is a sectional view as taken on line 8—8 of FIG. 7.

Catheter 50, as shown in FIGS. 6–8, is an alternate embodiment of a balloon dilation catheter of the present invention. Catheter 50 includes a manifold 52, a shaft 54, and a balloon member 58.

Manifold 52 defines the proximal portion of catheter 50 and is an elongated rigid member preferably formed of an inflexible plastic material. A thumbscrew 60 is threadably mounted on a threaded proximal end 62 of the manifold 52. Associated with the thumbscrew 60 is a deformable member (O-ring 64) which constricts onto a guide wire 56 which is disposed through the manifold 52 and the thumbscrew 60. Thus, the O-ring 64 restricts longitudinal movement of the guide wire 56 relative to manifold 52 and catheter 50 and provides a fluid seal between the wire 56 and manifold 52.

A proximal portion 65 of an inner tube 70 is disposed within a central bore of manifold 52, and extends distally therefrom beyond a distal end of the manifold 52 to define a guide wire lumen 72. The inner tube 70 is made of a plastic material, preferably polyethylene. An inner surface of the inner tube 70 is preferably coated with a lubricous material such as polytetrafluoroethylene or polydimethylsiloxane to facilitate the movement of the guide wire 56 therethrough. A purge port 66 is provided on the manifold 52 adjacent the proximal end 65 of the inner tube 70. Together, the thumbscrew 60, O-ring 64, manifold 52 and purge port 66 define a proximal end of the guide wire lumen 72.

The purge port 66 is adapted for connection to a fluid delivery device (not shown) such as a syringe which provides fluid under pressure to the guide wire lumen 72. The thumbscrew 60 and O-ring 64 cooperate to provide a fluid seal at the proximal end of the guide wire lumen 72 when the thumbscrew 60 is tightened.

Shaft 54 is defined by an outer tube 74 which is disposed about the inner tube 70 and extends coaxially therewith from the distal end of the manifold 52. Thus, there is defined an annular inflation lumen 80 between the inner tube 70 and the outer tube 74. The proximal end of the inflation lumen 80 is associated with a balloon inflation port 78 which is adapted for connection to an inflation device (not shown). The outer tube 74 extends distally from the manifold 52 to a distal waist segment 75 formed about the distal end thereof. The inner tube 70 extends distally some distance beyond the distal waist segment 75 of outer tube 74. The outer tube 74 is made from a plastic material, preferably polyethylene and is coated with a lubricous coating on its outer surface to facilitate its insertion through a guide catheter and a patient's vascular system. Preferably, the lubricous coating is polyterafluoroethylene or polydimethylsiloxane.

The balloon member 58 is preferably formed of a polymer material such as polyolefin copolymer and comprises a balloon lip segment 82, a distensible balloon segment 84 and a small diameter distal segment 86. The balloon lip segment 82 is attached to the distal waist segment 75 of the outer tube 74, preferably by an epoxy bond. The distensible balloon segment 84 extends distally from the balloon lip segment 82 coaxially disposed about the inner tube 70. The length of the inner tube 70 extending beyond the distal waist segment 75 of the outer tube 74 is designed to coincide with the length of the balloon member 58 such that the small diameter distal segment 86 of the balloon member 58 is bonded to a distal end of the inner tube 70. The balloon member 58 is thus sealably secured to the outer tube 74 (proximally) and inner tube 70 (distally) to define a balloon cavity 87 therebetween. A balloon member inlet port 79 for the balloon cavity 87 is defined by the extension of the inflation lumen 80 therethrough. Thus, the balloon inflation port 78, the inflation lumen 80, and the balloon member inlet port 79 cooperate to provide a path for the inflation medium to the balloon member 58.

A vent tube 92 is disposed within the balloon cavity 87 to define a vent lumen 100 therein. The vent tube 92 is preferably formed of a polyimide material. A distal end 93 (FIG. 7) of the vent tube 92 is positioned proximate to the small diameter distal segment 86 of the balloon member 58 and defines an inlet 94 to the vent lumen 100. The vent tube 92 extends proximally therefrom to an outlet 95 at a proximal end 96 of the vent tube 92. The outlet 95 of the vent tube 92 is positioned adjacent to a radially placed hole 97 through the inner tube 70 and is bonded thereto to define a proximal entry port 98 for gases to flow from the vent lumen 100 into the guide wire lumen 72. Preferably, the radially placed hole 97 through the inner tube 70 is distal from and adjacent to the distal waist segment 75 of the outer tube 74. Thereby, a vent path having a first proximally directed portion and a second distally directed portion is defined to purge the catheter 50 of unwanted gases. The vent lumen 100 of the vent tube 92 defines the first proximally directed portion (arrow 102, FIG. 7) of the vent path and the guide wire lumen 72 defines the second distally directed portion (arrow 103, FIG. 7) of the vent path.

Prior to insertion of catheter 50 (FIGS. 6–8) into the patient, the catheter 50 is purged of unwanted gases by introducing an inflation medium through the balloon inflation port 78 into and through the inflation lumen 80 to the balloon member 58 while holding the distal tip of the catheter in a most vertical position. The inflation medium (liquid) thus displaces the existing air and other gases within the balloon cavity 87. The displaced gases are forced out of the balloon cavity 87 into the inlet 94 and through the vent lumen 100. Thereafter, the gases are introduced into the guide wire lumen 72 through the proximal entry port 98 to be ultimately flushed out of the guide wire lumen 72 of the catheter 50. As described with reference to FIGS. 1-5, the gases are ultimately flushed from the catheter by the introduction of a flush solution (saline) into the guide wire lumen 72 from purge port 66. Thereafter, the balloon member 58 is deflated by the application of a vacuum to prepare it for introduction into the patient. The relative viscosities of the unwanted gases and inflation medium forced therethrough and the relationship of the viscosity of the inflation medium compared to the diameter and length of the vent tube 92 assures that the unwanted gases will be forced into and through the vent tube 92 along with a small plug of inflation medium. A vent 92 having a 0.0020 inches internal diameter and a length of approximately 2.5 centimeters (0.78–1.182 inches) achieves the desired result. Furthermore, as previously described with reference to FIGS. 1-5, the relative strength of the vacuum applied to finally deflate the balloon member 58 of inflation medium is less than the inflation pressure so the plug of inflation medium within the vent tube 92 remains and the purged gases are not significantly drawn back into the balloon cavity 87 upon application of the deflation vacuum.

Figure 9:
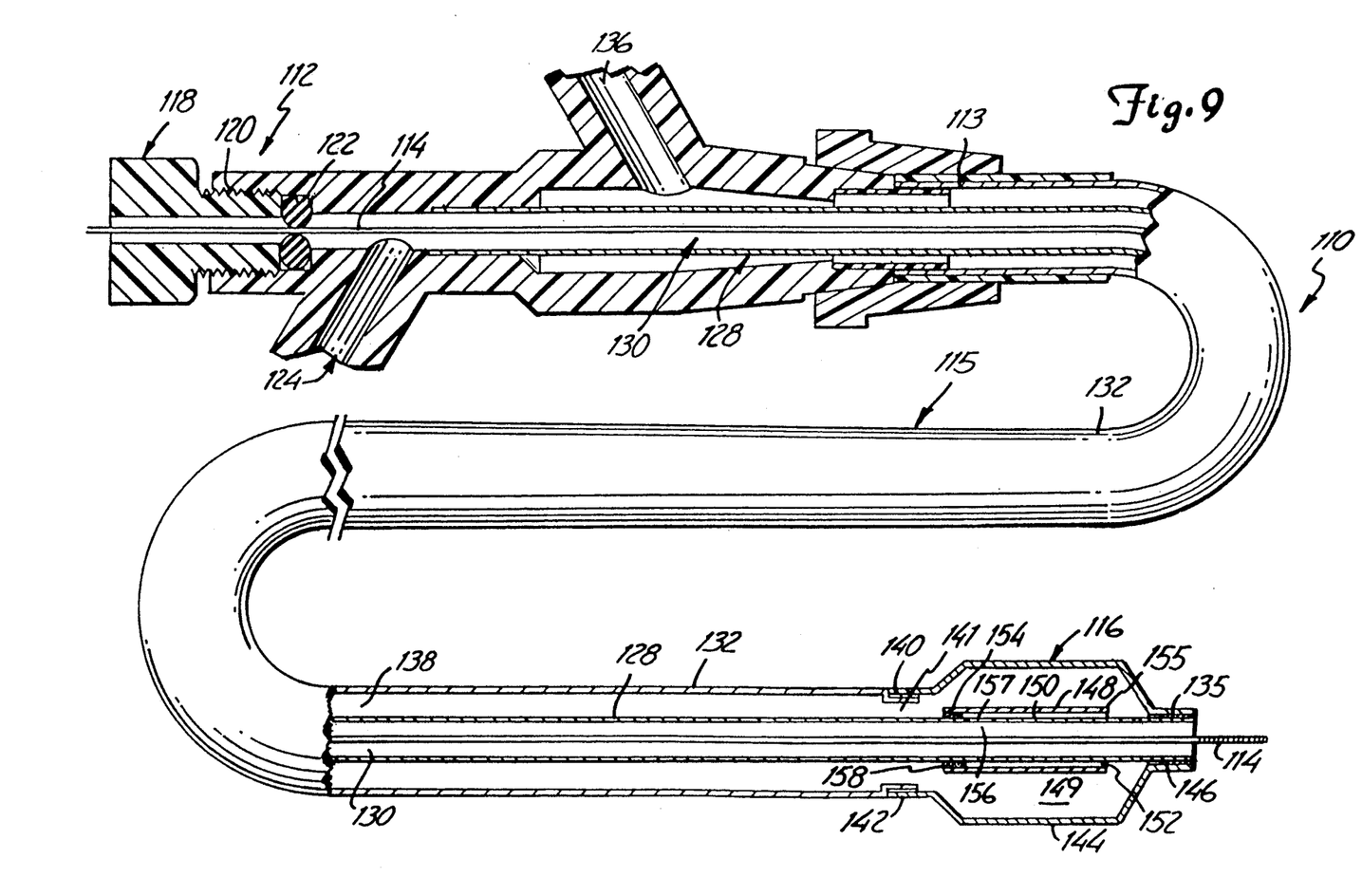
FIG. 9 is a side view, partially in section, of another embodiment of the balloon dilatation catheter of the present invention with a balloon shown in an inflated condition.
Figure 10:
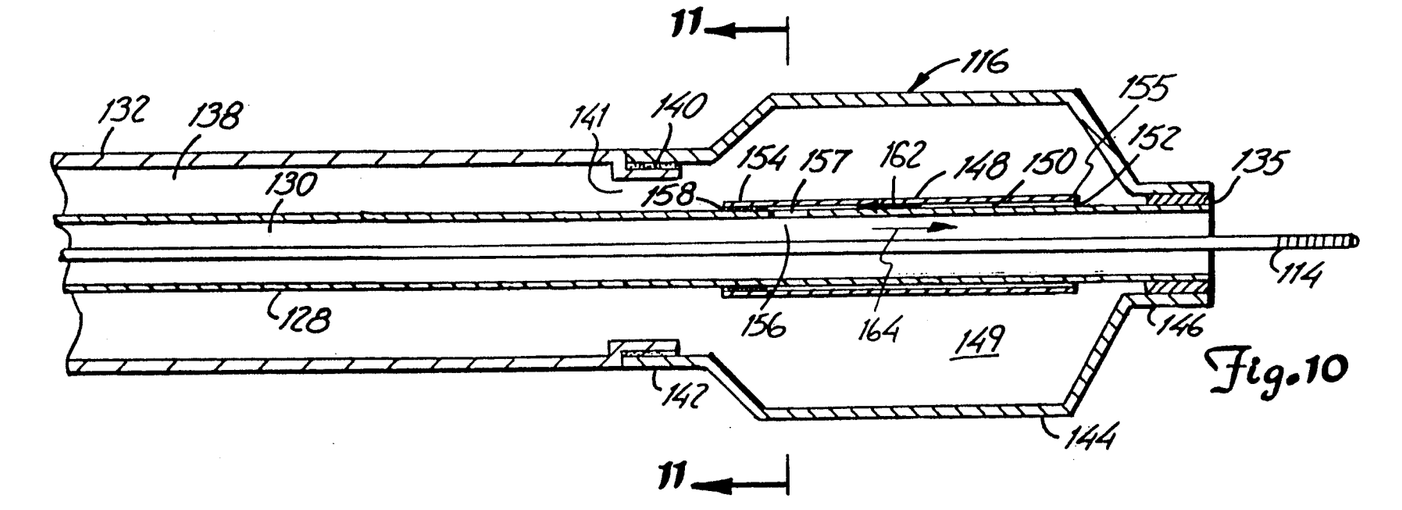
FIG. 10 is an enlarged side sectional view of a distal portion of the balloon dilatation catheter of FIG. 9 with the balloon shown in an inflated condition.
Figure 11:
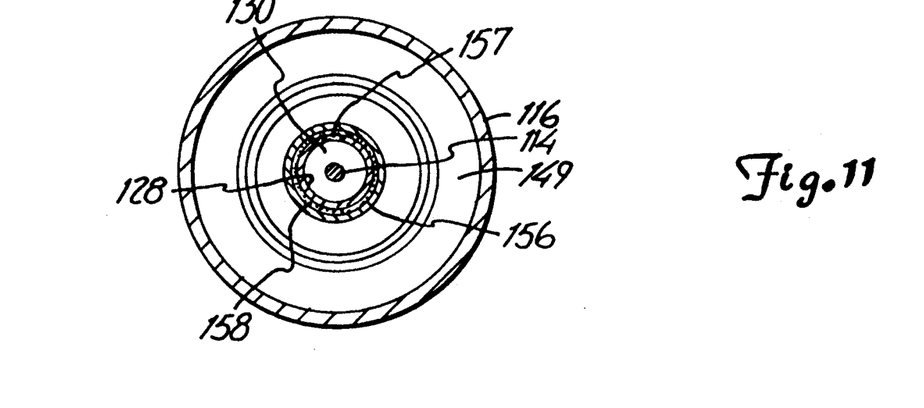
FIG. 11 is a sectional view as taken on line 11—11 to FIG. 10.

Another embodiment of a distensible balloon catheter of the type contemplated by the present invention is shown in FIGS. 9-11. Catheter 110 shown in FIGS. 9-11 comprises a manifold 112, a shaft 115 and a balloon member 116.

Manifold 112 defines the proximal portion of catheter 110 and is an elongated rigid member preferably formed of an inflexible plastic material. A thumbscrew 118 is threadably mounted on a threaded proximal end 120 of the manifold 112. A guide wire 114 is disposed through manifold 112 and the thumbscrew 118 associated therewith. An O-ring 122 is mounted adjacent to the thumbscrew 118. When the thumbscrew 118 is tightened, it applies pressure to the O-ring 122 to constrict onto the guide wire 114 to restrict longitudinal movement of the guide wire 114 relative to the manifold 112 and thumbscrew 118 and to provide a liquid tight seal at a proximal end of the manifold 112.

A purge port 124 is positioned distally from and adjacent to the thumbscrew 118. An inner tube 128 is disposed through a central bore of the manifold 112 and has a proximal end mounted distally of and adjacent to the purge port 124. The inner tube 128 extends distally therefrom to define a guide wire lumen 130 through which the guide wire 114 is maintained. Together, the thumbscrew 118, O-ring 122, manifold 112 and purge port 124 define a proximal end of the guide wire lumen 130. A distal end segment 135 defines the distal end of the inner tube 128. The inner tube 128 is preferably formed of a polymer material such as polyethylene and has an interior surface coated with a lubricous material such as polytetrafluoroethylene or polydimethylsiloxane to facilitate movement of the guide wire 114 therethrough.

An elongated flexible outer tube 132 is secured to a distal end 113 of manifold 112 and is coaxially disposed about the inner tube 128 and extends distally therewith. The coaxial placement of the inner tube 128 and the outer tube 132 defines an annular inflation lumen 138 therebetween. A distal waist segment 140 of outer tube 132 is positioned some distance proximal of the distal end segment 135 of the inner tube 128 as shown in FIGS. 9 and 10. Outer tube 132 thus defines the shaft 115 for catheter 110 and is formed of polyethylene and is preferably coated with a lubricous coating such as polytetrafluoroethylene or polydimethylsiloxane which provides a slippery surface to aid in the insertion and removal of the catheter 110 through a guide catheter and a patient's vascular system.

The balloon member 116 is preferably formed of polyolefin copolymer and has a balloon lip segment 142, a distensible balloon segment 144 and a small diameter distal segment 146. The balloon member 116 is affixed at the balloon lip segment 142 to the distal waist segment 140 of the outer tube 132 and at the distal segment 146 to the distal end 135 of inner tube 128, by an adhesive seal such as epoxy. Thus, there is defined a sealed balloon cavity 149 therein. Manifold 112 includes a balloon inflation port 136 adapted for connection to an inflation device (not shown). The balloon inflation port 136 is cooperatively associated with the inflation lumen 138 to introduce fluid under pressure into the inflation lumen 138. Pressurized fluids are forced through the inflation lumen 138 into the balloon cavity 149 at a balloon member inflation port 141 defined at the distal waist segment 140 of outer tube 132.

A sheath or sleeve 148 having a proximal end 154 and a distal end 155 is coaxially disposed about inner tube 128 in close relation thereto (preferably, within the distensible balloon segment 144) to define an annular vent lumen 150 therebetween. The distal end 155 of sheath 148 is positioned adjacent the distal segment 146 of the balloon member 116 and defines an inlet 152 to the vent lumen 150. A radially placed hole 157 through inner tube 128 is preferably positioned distal of and adjacent to the balloon lip segment 142. The sheath 148 extends proximally beyond the hole 157 of inner tube 128 to provide a surface for an annular bond 158 (e.g., epoxy) to affix the sheath 148 to the inner tube 128. The annular bond 158 restricts the proximal direction of flow of gases or liquid through the vent lumen 150 beyond hole 157. The sheath 148 is formed of a plastic material, preferably, polyimide or polyethylene. The cooperation of the sheath 148, the annular bond 158 and the radially placed hole 157 defines a proximal entry port 156 from the vent lumen 150 into the guide wire lumen 130. Thereby, a vent path having a first proximally directed portion and a second distally directed portion is defined to purge the catheter 110 of unwanted gases. The vent lumen 150 defines the proximally directed portion (arrow 162, FIG. 10) of the vent path and the guide wire lumen 130 defines the distally directed portion (arrow 164, FIG. 10) of the vent path. The balloon member 116 is purged of unwanted gases by first directing gases proximally and then distally through the vent path.

Preferably, the sheath 148 is constructed to define a 0.0005 inch diametric clearance between an inner surface of the sheath 148 and an outer surface of inner tube 128. The 0.0005 inch diametric clearance therebetween defines the annular vent lumen 150. For example, for a catheter construction having an inner tube 128 with an inner diameter dimension of 0.016 inch and an outer diameter dimension of 0.019 inch, the sheath 145 preferably would have an inner diameter dimension of 0.0195 inches and a length of approximately 1 cm (0.394 inches). In such a construction the radially placed hole 157 would have approximately a 0.003 inch diameter.

As previously described, the catheter 110 is purged of unwanted gases prior to its introduction into the patient. An inflation medium is introduced into the inflation lumen 138 via inflation port 136 and travels therethrough to the balloon member inflation port 141 where it is introduced into the balloon member 116. The introduction of inflation medium causes unwanted gases trapped therein to be forced out of the balloon cavity 149 into the vent lumen 150 via inlet 152. Unwanted gases are directed through vent lumen 150 for release at outlet 156 into the guide wire lumen 130. Thereafter, a flush solution is introduced via purge port 124 through the guide wire lumen 130 to force the unwanted gases from the catheter 110. Finally, a vacuum is applied across the inflation lumen 130 to rid the balloon 116 of inflation medium for use and to reduce the balloon profile for introduction into the patient.

Again, the relative viscosities of the unwanted gases and inflation medium forced through the inflation lumen 138 and the relationship of the viscosity of the inflation medium relative to the cross sectional dimension and length of the annular vent lumen 150 defined by sheath 148, assure that unwanted gases will be forced into and through the vent lumen 150 along with a small plug of inflation medium. Furthermore, as previously described, the relative strength of a vacuum applied to deflate the balloon 116 is less than the inflation pressure so that the plug of inflation medium is not released and drawn back into the balloon cavity 149 when the balloon member 158 is deflated for use. Since the plug of inflation medium is not released from the vent lumen 150, unwanted gases are not drawn back into the balloon cavity 149 upon application of the deflation vacuum.

It should be noted that for all illustrated embodiments of the present invention, the drawings are not to scale. For example, the vent lumens are shown greatly enlarged and exaggerated for clarity.

The catheter of the present invention has considerable advantages over those of the prior art. The vent lumen of the catheter of the present invention has an inlet positioned proximate to the distal end of the balloon member to assure that all gases trapped along the catheter shaft and within the balloon member are forced into the vent lumen. The vent lumen defines a first portion of a vent path. Another portion of the vent path is within the guide wire lumen (for ease of manufacture and efficiency in design) and provides the path for expunging gases from the vent lumen outside the catheter.

Although the present invention has been described with reference to several embodiments, workers skilled in the art will recognize that changes may be made in form and detail without departing from the spirit and scope of the invention. For example, in the embodiments of FIGS. 1-5, the length of the second inner tube determines the length of the proximally directed portion of the vent path. As shown in FIGS. 1-5, the second inner tube has its proximal end positioned proximally from the lip segment of the balloon member. Alternatively, the second inner tube can be constructed so that its proximal end is positioned adjacent to or distally from the lip segment of the balloon member. Such an arrangement is used if a shorter proximally directed length for the vent path is desired, or if a longer balloon member is used. Similarly, the initial vent means shown in FIG. 6 (tube 92) and FIG. 9 (sheath 148) can extend proximally beyond the balloon and into the catheter shaft. The length of the vent path can be shortened or lengthened by controlling the cross sectional area of the vent path or the resistance to liquid flow due to geometry of the vent path. For example, the length of the vent path can be shortened by decreasing the cross sectional area of the vent path.

The preferred embodiments herein disclosed are based upon the use of a 0.014 inch guide wire. Catheters could be designed around various sized guide wires with subsequently different dimensions for the purge system members while achieving a similar result.

What is claimed is:

1. A balloon catheter comprising:
   a guide wire lumen having a proximal portion and a distal portion, the proximal portion being defined by only a first inner tube and the distal portion being defined by a second inner tube, with the second inner tube being positioned within a distal section of the first inner tube to define a vent lumen therebetween;
   an annular inflation lumen defined by an outer tube positioned over the first inner tube; and
   a balloon member having a proximal portion connected to a distal end of the outer tube so that the balloon member interior is in fluid communication with the inflation lumen, and having a distal portion connected to a distal end of the second inner tube, which is spaced distally from a distal end of the first inner tube so that the balloon member interior is in communication with the vent lumen between the first and second inner tubes with the vent lumen being of size to permit the flow of gas therethrough but to significantly inhibit the flow of liquid therethrough.

2. The balloon catheter of claim 1, wherein the first inner tube is fixed relative to longitudinal movement with respect to the outer tube.

3. The balloon catheter of claim 2, wherein the first inner tube and the outer tube are fixed relative to one another only at their respective proximal ends.

4. The balloon catheter of claim 1, wherein the proximal portion of the balloon member and the distal end of the outer tube are connected with an adhesive seal.

5. The balloon catheter of claim 1, wherein the distal portion of the balloon member and the distal end of the second inner tube are connected with an adhesive seal.

6. The balloon catheter of claim 1, wherein the distal end of the outer tube is distal to a proximal end of the second inner tube.

7. The balloon catheter of claim 1, wherein the distal end of the first inner tube is distal to the distal end of the outer tube.

8. The balloon catheter of claim 1, wherein the distal end of the first inner tube is closely spaced from the distal portion of the balloon member to define an inlet for the vent lumen.

9. The balloon catheter of claim 1, wherein a proximal end of the second inner tube is proximal of the proximal portion of the balloon member.

10. The balloon catheter of claim 1, wherein the vent lumen is an annular vent lumen.

11. The balloon catheter of claim 1, wherein an outer surface of the outer tube has a lubricous coating.

12. The balloon catheter of claim 11, wherein the lubricous coating is polytetrafluoroethylene.

13. The balloon catheter of claim 11, wherein the lubricous coating is polydimethylsiloxane.

14. The balloon catheter of claim 1, wherein the second inner tube is composed of polyimide.

15. The balloon catheter of claim 1, wherein the second inner tube is composed of polyethylene.

16. The balloon catheter of claim 1, wherein an inner surface of second inner tube has a lubricous coating.

17. The balloon catheter of claim 16, wherein the lubricous coating is polytetrafluoroethylene.

18. The balloon catheter of claim 16, wherein the lubricous coating is polydimethylsiloxane.

19. The balloon catheter of claim 1, wherein the first inner tube is composed of polyethylene.

20. The balloon catheter of claim 1, wherein an inner surface of the first inner tube has a lubricous coating.

21. The balloon catheter of claim 20, wherein the lubricous coating is polytetrafluoroethylene.

22. The balloon catheter of claim 20, wherein the lubricous coating is polydimethylsiloxane.

23. The balloon catheter of claim 1, wherein a portion of the first inner tube is bonded to the second inner tube.

24. The balloon catheter of claim 23, wherein a distal end of the first inner tube is bonded to the second inner tube.

25. A multilumen balloon catheter having a guide wire lumen, an inflation lumen and a distally placed balloon member having its interior in fluid communication with the inflation lumen, the improvement which comprises:
  a vent path separate from the balloon interior for use in purging the balloon member of gas which has a first proximally directed portion and a second distally directed portion, with the second portion being defined by a distal segment of the guide wire lumen.

26. A multilumen balloon catheter having a guide wire lumen, an inflation lumen and a distally placed balloon member having its interior in fluid communication with the inflation lumen, the improvement which comprises:
  a vent for purging the balloon member of gas which includes:
    means for directing purged gas out of the balloon interior and then proximally from a distal end of the balloon member to an entry port into the guide wire lumen; and
    means for directing the purged gas distally from the entry port through the guide wire lumen and out of the balloon catheter.

27. The balloon catheter of claim 26 wherein the entry port into the guide wire lumen is proximal of the balloon member.

28. The balloon catheter of claim 26 wherein at least a distal portion of the guide wire lumen is defined by a tube and wherein the means for directing purged gas proximally comprises:
  an elongated sheath extending about the tube defining the guide wire lumen, and over the entry port therethrough, the sheath being spaced radially from the tube to define a vent lumen between the tube and the sheath which opens to the balloon interior at a distal end of the sheath and opens to the guide wire lumen through the entry port at a proximal end of the sheath, with the sheath having its proximal end closed and affixed to the tube.

29. The balloon catheter of claim 28 wherein the sheath is composed of polyethylene.

30. The balloon catheter of claim 28 wherein the sheath is composed of polyimide.

31. The balloon catheter of claim 26 wherein the entry port is located along a distal portion of the guide wire lumen within the balloon member.

32. The balloon catheter of claim 26 wherein the means for directing purged gas proximally comprises:
  an elongated vent tube in the balloon interior having an inlet adjacent to a distal end of the balloon member and an outlet coupled to the entry port in the guide wire lumen to permit purged gas to flow proximally from the inlet through the vent tube and into the guide wire lumen.

33. The balloon catheter of claim 32 wherein the vent tube is composed of polyimide.

34. A method for purging gas from a balloon catheter having a guide wire lumen, an inflation lumen and a distally placed balloon member having its interior in fluid communication with the inflation lumen, the method comprising the steps of:
  directing gas out of the balloon member interior and then proximally from a distal end of the balloon member to an entry port into the guide wire lumen; and
  directing the gas distally from the energy port through the guide wire lumen and out of the balloon catheter.

35. The method of claim 34, and further comprising the step of:
  urging a distal portion of the balloon member distally relative to the inflation lumen to create an inlet from the balloon member interior into a vent lumen.

36. A balloon catheter comprising:
  a guide wire lumen having a proximal portion and a distal portion, the proximal portion being defined by a first inner tube having a proximal end and a distal end, the distance therebetween defining an extent of the first inner tube, and the distal portion being defined by a second inner tube having a proximal end and a distal end, the distance between the proximal end of the second inner tube and the distal end of the second inner tube being shorter than the extent of the first inner tube, and the second inner tube being positioned within a distal section of the first inner tube to define a vent lumen therebetween, the vent lumen extending only along a distal extent of the catheter between the distal end of the first inner tube and the proximal end of the second inner tube;
  an annular inflation lumen defined by an outer tube positioned over the first inner tube; and
  a balloon member having a proximal portion connected to a distal end of the outer tube so that the balloon member interior is in fluid communication with the inflation lumen, and having a distal portion connected to the distal end of the second inner tube, which is spaced distally from the distal end of the first inner tube so that the balloon member interior is in communication with the vent lumen between the first and second inner tubes with the vent lumen being of size to permit the flow of gas therethrough but to significantly inhibit the flow of liquid therethrough.

37. A balloon catheter comprising:
  a guide wire lumen having a proximal portion and a distal portion, the proximal portion being defined by only a first inner tube and the distal portion being defined by a second inner tube, with the second inner tube being aligned generally coaxially within a distal section of the first inner tube and having a distal segment which extends distally beyond a distal end of the first inner tube so that a vent lumen is defend between the first and second inner tubes along the distal section of the first inner tube;
  an annular inflation lumen defined by an outer tube positioned over the first inner tube; and
  a balloon member having a proximal portion connected to a distal end of the outer tube so that the balloon member interior is in fluid communication with the inflation lumen, and having a distal portion connected to a distal end of the second inner tube, which is spaced distally from a distal end of the first inner tube so that the balloon member interior is in communication with the vent lumen between the first and second inner tubes with the vent lumen being of size to permit the flow of gas therethrough but to significantly inhibit the flow of liquid therethrough.

* * * * *

UNITED STATES PATENT AND TRADEMARK OFFICE
CERTIFICATE OF CORRECTION

PATENT NO. : 5,176,698

DATED : January 5, 1993

INVENTOR(S) : MATTHEW M. BURNS, DANIEL O. ADAMS
CHARLES L. EUTENEUER

It is certified that error appears in the above-identified patent and that said Letters Patent is hereby corrected as shown below:

On the Title Page,
   delete [54] VENTED DILATATION CATHETHER AND METHOD FOR VENTIN insert [54] VENTED DILATATION CATHETER AND METHOD FOR VENTING

Col. 14, line 1, delete "energy", insert "entry"

Col. 14, line 50, delete "defend", insert "defined"

Signed and Sealed this

Twenty-sixth Day of October, 1993

Attest:

BRUCE LEHMAN

*Attesting Officer*  *Commissioner of Patents and Trademarks*